United States Patent [19]

Horlington

[11] 4,425,346

[45] Jan. 10, 1984

[54] PHARMACEUTICAL COMPOSITIONS

[75] Inventor: Michael Horlington, Bishops Stortford, England

[73] Assignee: Smith and Nephew Associated Companies Limited, United Kingdom

[21] Appl. No.: 342,655

[22] Filed: Jan. 25, 1982

Related U.S. Application Data

[63] Continuation-in-part of Ser. No. 287,356, Jul. 27, 1981.

[30] Foreign Application Priority Data

Feb. 9, 1981 [GB] United Kingdom ............ 8103917
Mar. 18, 1981 [GB] United Kingdom ............ 8108537

[51] Int. Cl.³ .................. A61K 31/505; A61K 31/52
[52] U.S. Cl. ..................................... 424/253; 424/251
[58] Field of Search ............................. 424/251, 253

[56] References Cited

U.S. PATENT DOCUMENTS

| | | | |
|---|---|---|---|
| 3,081,230 | 3/1963 | Weinstock et al. | 424/251 |
| 3,870,791 | 3/1975 | Haddad et al. | 424/251 |
| 4,118,492 | 10/1978 | Voelger et al. | 424/251 |
| 4,187,307 | 2/1980 | Paris et al. | 424/251 |
| 4,285,947 | 8/1981 | Higuchi et al. | 424/251 |

FOREIGN PATENT DOCUMENTS 932256 7/1963 United Kingdom.
1009477 11/1965 United Kingdom.

OTHER PUBLICATIONS

Martindale–The Extra Pharmacopoeia, 27th Ed. (1977) pp. 569–570.
Pteridines XII Structure-Activity Relationships of Some Pteridine Diuretics, Weinstock et al., J. Med. Chem. 1968 11 573-579.
2,4,7-Triamino-6-Ortho-Substituted Aryl Pteridines, A New Series of Potent Antimalarial Agents, Osdene et al., J. Med. Chem. 1967 10 pp. 431-433.

Primary Examiner—Douglas W. Robinson
Attorney, Agent, or Firm—Jacobs & Jacobs

[57] ABSTRACT

The present invention relates to pharmaceutical compositions adapted for topical administration to the eye and to their preparation and use. More specifically this invention relates to anti-glaucoma ophthalmic compositions containing tetraazabicyclic compounds of the formula:

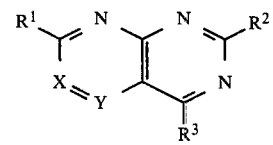

wherein $R^1$, $R^2$, $R^3$, X and Y are hereinafter defined and to the preparation and use of such compositions.

61 Claims, No Drawings

PHARMACEUTICAL COMPOSITIONS

This is a continuation-in-part of application U.S. Ser. No. 287,356 filed July 27, 1981 and entitled "Pharmaceutical Composition."

Glaucoma is a degenerative disease of the eye manifest inter alia by an elevated intra-ocular pressure in the eye. Ocular hypertension, that is the condition of elevated intra-ocular pressure, is believed by many authorities to represent an early phase in the onset of glaucoma. One method of treatment of ocular hypertension and glaucoma is to administer to the subject a pharmacologically active compound capable of reducing the intra-ocular pressure. A number of compounds presently employed to treat ocular hypertension and glaucoma are not entirely satisfactory due at least in part to side effects such as pupil contraction and the like. Clearly it would be desirable to provide an agent which could be applied topically to treat ocular hypertension and glaucoma without an unacceptable level of such side effects. It has now been found that the optical administration of tetraazabicyclic compounds to the eye can reduce the intra-ocular pressure therein without producing an unacceptable level of side effects such as pupil constriction.

It has now been found that the topical administration of other tetraazabicyclic compounds to the eye results in a lowering of intra-ocular pressure and that this occurs without systemic side effects such as diuresis and without local side effects such as pupil constriction.

Accordingly the present invention provides a pharmaceutical composition adapted for administration to the eye which composition contains a compound of the formula (I):

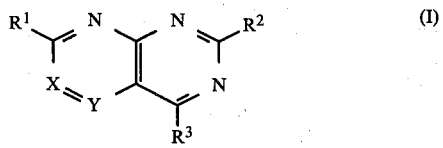

wherein X=Y is CR=N or N=CR where at least two of R, $R^1$, $R^2$ and $R^3$ are amino groups and the other groups of R, $R^1$, $R^2$ and $R^3$ are hydrogen atom, lower alkyl, aryl, carboxamido or lower alkoxycarbonyl groups; together with a carrier therefor.

Compounds of the formula (I) may be prepared in known manner, for example as in the following series of papers, (a) Spickett and Timmis, J. Chem. Soc. 1954, 2887–95; (b) Pachter and Nemeth, J. Org. Chem. 1963, 28 1187–91; (c) Pachter, ibid 1963, 28 1191–96; (d) Pachter and Nemeth, ibid 1963 28 1203–06; (e) Weinstock et al, J. Med. Chem. 1968, 11 542–48; (f) Weinstock et al, ibid, 1968, 11 549–56; (g) Weinstock et al, ibid 1968, 11 557–60; (h) Weinstock and Dunoff, ibid 1968, 11 565–68; (i) Weinstock et al, ibid 1963, 11 618–20; (j) Mallette et al, J. Am. Chem. Soc. 1947, 69 1814. The diuretic properties of such when given orally to rats and dogs is described by Weinstock et al in J. Med Chem. 1963, 11 573–79. However this paper contains no suggestion that such pteridine derivatives may be applied topically to the eye and no suggestion is made that such pteridine derivatives may be useful in the treatment of glaucoma. The preparation of some further compounds of the formula (I) is described in Graboyes et al, J. Med Chem. 1963 11 568–73. The diuretic properties of these compounds is described in Weinstock et al in J. Med. Chem. 1963, 11 573–79. This paper contains no suggestion that such compounds may be applied topically to the eye and no suggestion is made that such compounds may be useful in the treatment of glaucoma.

Compositions suitable for topical application to the eye containing 2,4,7-triamino-6-phenyl-pteridine are described in our co-pending U.S. applications, Ser. Nos. 287,356 and 328,729 which are incorporated herein by cross-reference.

When used herein the term lower means a group of 1, 2 or 3 carbon atoms and most aptly refers to a group containing 1 carbon atom.

In compounds of the formula (I) as hereinbefore defined most aptly $R^3$ is an amino group.

In compounds of the formula (I) as hereinbefore defined most aptly X=Y is a $CR^4$=N group where $R^4$ is a hydrogen atom, a lower alkyl, an aryl or a carboxamido group.

Thus favoured compositions contain a compound of formula (II):

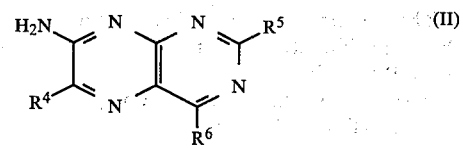

wherein either $R^5$ and $R^6$ are amino groups or one of $R^5$ and $R^6$ is an amino group and the other is a hydrogen atom, a lower alkyl or an aryl group; and $R^4$ is a hydrogen atom, a lower alkyl, an aryl or a carboxamido; together with a carrier therefor.

Particularly apt compositions contain a compound of formula (III):

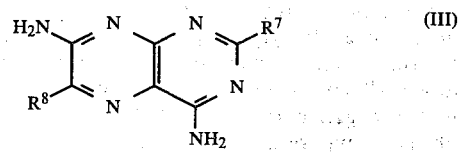

wherein $R^8$ is a hydrogen atom, a lower alkyl, an aryl, a lower alkoxycarbonyl or carboxamido group and $R^7$ is a phenyl group or a phenyl group substituted by a fluorine, chlorine or bromine atom or by a lower alkyl, lower alkoxy, amino, nitro, hydroxyl or sulphated hydroxyl group; together with a carrier therefor.

Aptly $R^7$ is a phenyl group optionally substituted in the 3 or 4 position.

Preferably $R^7$ is a phenyl group.

From the foregoing it will be appreciated that highly favoured compounds for use in this invention include 2-phenyl-4,7-diamino-6-carboxamido-pteridine and the ethyl ester of 2-phenyl-4,7-diamino-pteridine-6-carboxylic acid.

Particularly suitable compositions contain a compound of formula (IV):

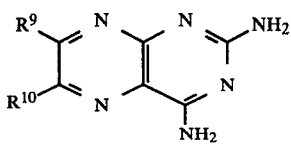

wherein $R^9$ is a hydrogen atom, an amino group, a lower alkyl group or an aryl group and $R^{10}$ is a hydrogen atom, a lower alkyl group, an aryl group or a carboxamido group; together with a carrier therefor.

Aptly $R^9$ is an amino group or a methyl group.

Preferably $R^9$ is an amino group.

Aptly $R^{10}$ is a phenyl group optionally substituted by a fluorine, chlorine or bromine atom or by a lower alkyl or in any position by lower alkoxyl, amino, nitro, hydroxyl or sulphated hydroxyl group.

Preferably $R^{10}$ is a phenyl group substituted as hereinbefore described or a methyl group.

From the foregoing it will be appreciated that highly preferred compounds for use in this invention include 2,4,7-triamino-6-(4-nitrophenyl)-pteridine, 2,4,-triamino-6-(4-hydroxyphenyl)-pteridine, the hemi-sulphate ester of 2,4,7-triamino-6-(4-hydroxyphenyl)-pteridine and 2,4-diamino-6,7-dimethyl-pteridine.

The preferred compound for use in this invention is the hemi-sulphate ester of 2,4,7-triamino-6-(4-hydroxyphenyl)-pteridine.

A second group of suitable compounds are those of formula (I) in which X=Y is N=CR namely compounds of formula (V) or a pharmaceutically acceptable salt thereof.

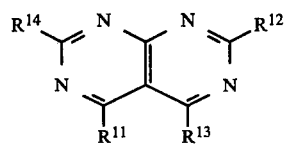

where at least two of $R^{12}$, $R^{13}$ and $R^{14}$ are amino groups and the other group is a hydrogen atom or a phenyl group or a phenyl group optionally substituted by a fluorine, chlorine or bromine atom or by a lower alkyl, lower alkoxy, amino, nitro, hydroxyl or a sulphated hydroxyl group and where $R^{11}$ is a hydrogen atom, a phenyl group, or a phenyl group optionally substituted by a fluorine, chlorine or bromine atom or by a lower alkyl, lower alkoxyl, amino, nitro, hydroxyl or sulphated hydroxyl group.

Preferably $R^{12}$ and $R^{13}$ are both amino groups.

Preferably $R^{14}$ is an amino group, a hydrogen atom or a phenyl group.

Preferably $R^{14}$ is an amino group.

Aptly $R^{11}$ is a hydrogen atom or a phenyl group.

Preferably $R^{11}$ is a phenyl group.

From the foregoing it will be appreciated that highly favoured compounds for use in this invention include 2,4,7-triamino-5-phenyl-pyrimido (4,5-d) pyrimidine.

Pharmaceutically acceptable salts of compounds of formula (V) include those with acids such as hydrochloric, sulphuric, orthophosphoric, acetic, gluconic, glutamic and lactic acids.

From the foregoing it will be appreciated that highly favoured compounds for use in this invention include 2,4,7-triamino-5-phenyl-pyrimido (4,5-d) pyridinium orthophosphate.

In order to be suitable for application to the eye the topical composition should be sterile, non-toxic and non-irritant to the eye.

From the foregoing the skilled worker will appreciate that this invention provides a sterile, non-irritant, non-toxic composition adapted for topical administration to the eye for the treatment of glaucoma which composition comprises a compound of formula (I) as hereinbefore described together with a carrier therefor.

Suitable forms of the composition include aqueous solutions, aqueous suspensions, oily solutions, oily suspensions, ointments, emulsions and sustained release implants. In general it is preferred to use aqueous solutions or aqueous suspensions for compositions of this invention. Such aqueous forms preferably also contain an agent which increases the amount of the compound of formula (I) in suspension (a suspending agent) or solution (a solubilising agent) as described hereinafter.

Most desirably the composition of this invention will be an aqueous solution.

Normally and preferably aqueous solutions and suspensions of the invention will contain tonicity adjusting agents, for example sodium chloride, potassium chloride, glycerol, propylene glycol, urea or dextrose to render the solution or suspension isotonic or substantially isotonic with tear fluid, that is to say, to give the compositions a tonicity equivalent to an aqueous solution containing from 0.8 to 1.1% of a sodium chloride and most suitably 0.9% sodium chloride. The use of sodium chloride or other ionic tonicity agents may render some solutions and suspensions unstable. In these cases it is preferred that a non-ionic tonicity adjusting agent such as glycerol or propylene glycol is used.

Aqueous suspensions of the invention will suitably contain from 0.01 to 5% of the compound, more suitably will contain from 0.05 to 2.5% of the compound and preferably from 0.1 to 1% for example 0.5% (% terms when used herein are expressed on a wt/v basis unles shown otherwise).

Aqueous solutions of the invention will contain an amount of the compound which will depend on the solubility of the specific compound used. Normally aqueous solutions may contain from 0.01 to 2% of the compound.

It is normally preferred in the treatment of glaucoma to employ an aqueous solution. Favourably the aqueous solutions of this invention will contain a solubilising agent such as polyvinyl pyrrolidone, polyalkylene glycol, non-ionic surfactants or a polyacrylic acid which has been lightly cross-linked with triallyl sucrose in combination with a non-ionic surfactant. An apt solubilising agent is polyvinyl pyrrolidone. Suitable polyvinyl pyrrolidones are those with a number average molecular weight below 40,000, more suitable are those with a number average molecular weight below 5000 and a particularly preferred polyvinyl pyrrolidone is one having a number average molecular weight of 2,500. Such a polyvinyl pyrrolidone is exemplified by Kollidon 12PF (trade mark of BASF). Suitably the amount of polyvinyl pyrrolidone present is from 0.5 to 55%, preferably is from 15 to 52% and most preferably is from 20 to 50%.

Alternatively the compounds useful in the present invention may be solubilised by employing a class of agents that neither unduly increases the viscosity of the solution nor unduly increases the surfactant properties of the solution. This class of agents which may be thus employed are water soluble xanthine derivatives.

Thus in a more favoured aspect this invention provides a sterile, non-irritant, non-toxic aqueous solution adapted for topical application to the eye for the treatment of glaucoma which composition comprises a compound of formula (I) as hereinbefore described and a solubilising xanthine and a carrier therefor.

The solubilising xanthine is normally a dimethyl xanthine which optionally may be substituted by a hydrophilic group or (less preferably) a methyl group. Most aptly the xanthine is a 1,3-dimethyl xanthine unsubstituted or substituted at the 7-position by a methyl group or more aptly substituted at the 7-position by a hydrophilic group such as a 2-hydroxypropyl group (thereby proxyphylline), a 2,3-dihydroxypropyl group (thereby dyphylline), a 2-hydroxyethyl group (thereby etophylline), a carboxymethyl group (thereby theophyllinylacetic acid), an N,N-diethylaminoethyl group (thereby etamiphylline) or the like. Less favourably the xanthine is a 3,7-dimethylxanthine unsubstituted or substituted at the 1-position for example pentoxyphylline.

Particularly apt solubilising xanthines are caffeine, proxyphylline and dyphylline. These agents may be present in any convenient solubilising amount, for example from 0.1 to 10% (or up to the solubility limit), more usually from 1 to 8%. Preferably the solution will contain from 2 to 7.5% of proxyphylline or diphylline.

The xanthine solubilising agent may be present as the sole solubilising agent or less aptly other solubilising agents such as those hereinbefore described may also be included.

The use of solubilising agents is particularly advantageous for the preparation of solutions of the sparingly soluble compounds It is desirable to provide aqueous solutions that are generally at a pH of not less than 4.5, more aptly not less than 6 and preferably at a pH of approximate neutrality that is pH 7. The pH of such solutions should also not in general be greater than 8.5 and preferably not greater than pH 8. It has been found that such solutions may be prepared by using solubilising agents such as a xanthine. If the solubilising agent is a xanthine a buffering agent may be present to maintain the pH from 5.0 to 8.0 and preferably 6.0 to 7.5 for example pH 7. Suitable buffering agents include mixtures of potassium dihydrogen phosphate and disodium hydrogen phosphate and other systems known to provide solutions having such pH values.

In certain circumstances it may be preferred to use a pharmaceutically acceptable salt of a compound of formula (I). Such salts include those with hydrochloric, sulphuric, orthophosphoric, acetic, gluconic, glutamic and lactic acids. In general these salts are prepared in situ and no not exist as true salts outside the formulation; that is the solutions of compounds of formula (I) may be rendered slightly acidic using such acids so that a salt is notionally formed.

Normally and preferably aqueous solutions of the invention will contain an ophthalmically acceptable preservative to maintain the sterility of the solutions during use. It is known in the art that certain preservatives are affected by the presence of surface active agents, viscosity increasing agents and the like and naturally such agents will be selected to be mutually compatible in the conventional manner. Particularly apt ophthalmically acceptable preservatives are antibacterially effective quaternary ammonium compounds such as benzalkonium salts, for example the chloride, benzethonium chloride, cetyl pyrridinium chloride and the like. The preferred quaternary ammonium compound is benzalkonium chloride. Suitably the amount of quaternary ammonium compound present is from 0.005 to 0.04%, more suitably is from 0.0075 to 0.025% and preferably from 0.01 to 0.02% of the composition.

In aqueous suspensions of compounds of formula (I) the compound will be dispersed evenly throughout. The compound will be in finely divided form. In this state of subdivision of the compound 99% of the particles are less than 30 microns in diameter and 90% are less than 10 microns in diameter. Most aptly the particles will have diameters in the range of 1 to 5 microns.

Generally the compositions of this invention will contain a suspending agent for the finely divided compound of formula (I). Suitable suspending agents include cellulosic or polysaccharide derivatives (such as hydroxyethyl cellulose, hydroxypropyl cellulose, carboxymethyl cellulose or xanthan gum) or water-soluble polymers (such as polyvinyl alcohol or polyvinyl pyrrolidone or a polyacrylic acid lightly cross-linked with triallyl sucrose). A most favoured suspending agent is a polyvinyl pyrrolidone as hereinbefore described. Suitably the suspension will contain from 5 to 55% of the polymer and preferably 20 to 50% of the polymer.

A second favoured suspending agent is a hydroxyethyl cellulose. Suitable hydroxyethyl celluloses are available as the Natrosols (trade mark of Hercules Inc.) and the Cellosizes (trade mark of Union Carbide Corp.). A 2% solution of suitable polymers at 25° C. has a viscosity of from 4500 to 6000 cps when measured on a Brookfield apparatus. A preferred hydroxyethyl cellulose is available as Natrosol 250M. Suitably the suspension will contain from 0.1 to 10% of the cellulose, more suitably 0.25 to 2.5% of the cellulose and preferably 0.5 to 1.0% of the cellulose.

Generally the aqueous suspension of the present invention will contain a surface active agent to encourage wetting of the surface of the particles of the finely divided compound by water, thus aiding even dispersion throughout the suspension. Favoured surface active agents are polyoxyethylated sorbitan fatty acid esters (commonly called Tweens) or polyoxypropylene-polyoxyethylene diol block copolymers (commonly called Pluronics). Particularly preferred is a polyoxypropylene-polyoxyethylene diol block copolymer of molecular weight 2900, having 40% of ethylene oxide units in the polymer, known as Pluronic L64. Suitably the amount of surface active agent present is from 0.01 to 5% and preferably from 0.02 to 0.2%.

Generally the aqueous suspensions will contain a ophthalmically acceptable preservative or bacterial agent. Such agents are subject to the same considerations of compatibility as described for aqueous solutions above. Suitable bacterial agents include phenylethanol, phenoxyethanol, chlorbutanol or thiomersal. A particularly preferred preservative is a combination of phenylethanol in an amount from 0.25 to 0.75% and thiomersal in an amount from 0.005 to 0.02%. A preferred combination is 0.5% phenylethanol with 0.01% thiomersal.

The pH values of the aqueous suspensions will be adjusted in a similar manner to that described hereinbefore with respect to aqueous solutions.

Oily suspensions of compounds of formula (I) include suspensions in solvents such as castor oil and such compositions will suitably contain from 0.01 to 5% of finely divided compound, more favourably 0.02 to 0.75% and most preferably 0.05 to 0.5% of the compound.

Ointments in accordance with the invention will comprise ointment bases suitable for topical application to the eye and contain suitably from 0.01 to 5% of the finely divided compound of formula (I).

Ocular implants may comprise a compound of formula (I) in a finely divided form in suitable soluble or insoluble material. Soluble forms for example where the finely divided compound is suspended in a polyvinyl alcohol film, dissolve and so do not need to be removed later, whereas the insoluble forms are removed from the eye after the medicament has diffused from the form. Suitably the ocular implant will contain from 0.01 to 5% of finely divided compound of formula (I).

The present invention also provides a method for reducing the intra-ocular pressure in the eye which comprises topically administering a compound of formula (I) to the surface of the eye in an amount effective to reduce the intra-ocular pressure therein. The compound of formula (I) will be present in a composition as herein-described.

Further the present invention provides a unit dose of a liquid topical composition of the invention having a volume from 0.01 to 0.08 ml (i.e. a drop of 10 to 80 microliters) and containing from 1 microgramme to 1.6 mg of a compound of formula (I) and more usually 0.02 to 0.05 ml and containing 2 microgrammes to 1 mg. of the compound.

The compositions of this invention are most aptly provided in a multidose container from which drops may be dispensed into the eye. Such containers are well known in the art for dispensing of liquid drops into the eye and such conventional containers may be employed. Most aptly such containers are adapted to hold 1 to 20 mls, more usually 2 to 12 mls and preferably 3 to 10 mls.

A favoured aspect of the present invention therefore comprises a container adapted to deliver drops of an aqueous solution or an aqueous suspension of this invention as hereinbefore described. A preferred container comprises a glass bottle having a screw cap. This screw cap being replaced by a screw cap carrying a drop forming portion when in use. A second preferred container comprises a plastic bottle, for example of a low density polyethylene, having an integral dispensing tip covered by a screw cap. Such preferred containers are adapted to hold 1 to 20 mls of the composition and preferably 3 to 10 mls of the composition, for example 5, 7.5 or 10 mls. A third preferred type of container adapted to deliver drops holding from 1 to 2.5 mls of composition is made from polypropylene or other heat stable material whereby the whole package may be filled and sealed prior to sterilisation by autoclaving.

The compositions of the present invention may be prepared by conventional means of mixing and blending.

Sterile compositions may be conveniently prepared by (a) sterilising the finely divided compound of formula (I) by dry heat over a period of time at elevated temperature, for example by heating to 160° for 1 hour, allowing the powder to cool and storing aseptically, (b) sterilising the liquid components of the composition by either filtration through a 0.22 micron cellulose ester membrane or subjecting the solution to heat and pressure such as autoclaving at 116° C. for 30 minutes under 10 psi pressure. The two sterile components are combined in the desired proportions under aseptic conditions and filled into sterile containers. The containers for delivering drops of sterile compositions of the invention are conventionally pre-sterilised and filled under aseptic conditions with the sterile composition using conventional metering pumps capable of delivering from 1 to 20 mls each filling cycle.

Alternatively for those compositions which are in the form of an aqueous solution, the solution may be formed by dissolving its components in distilled water and then sterilising the solution either by filtration through a 0.22 micron filter or by subjecting it to heat, for example by autoclaving at 116° C. for 30 minutes at 10 psi pressure. The sterile solution may be aseptically filled into pre-sterilised eye-dropper bottles in a conventional manner.

The compositions of this invention are non-irritant, that is they do not cause unacceptable irritation to the eye when applied topically. Most aptly the compositions are bland upon application.

The following Examples illustrate this invention:

EXAMPLE 1

2,4,7-Triamino-6-(2-bromophenyl)-pteridine suspension

A suspension of 2,4,7-triamino-6-(2-bromophenyl)-pteridine was prepared as follows:

| | |
|---|---|
| 2,4,7-Triamino-6-(2-bromophenyl)-pteridine | 0.5% w/v |
| *Polyvinyl pyrrolidone (molecular weight 2,500) | 50.0% w/v |
| Distilled water | to 100.0 ml. |

*The polyvinyl pyrrolidone was Kollidon PF12.

The polyvinyl pyrrolidone was dissolved in water (40 ml) and the 2,4,7-triamino-6-(2-bromophenyl)-pteridine suspended in this solution with stirring. The volume of the suspension was adjusted to 100 ml with distilled water with stirring.

The effect of this suspension on the ocular tension in the eyes of rabbits (New Zealand White/Male) was tested as follows. 50 microliters of the suspension was applied topically to both treated and untreated eyes was measured at 1, 2, 4 and 5 hours after the application of the suspension. The mean maximum fall in ocular tension in the treated eye of four rabbits was 3.4 mmHg (approximately) at 1 hour, in the untreated eye the mean maximum fall was 1.6 mmHg (approximately) at 1 hour.

The pupil diameter of both treated and untreated eye remained unchanged over the test period.

EXAMPLE 2

2,4,7-Triamino-5-phenylpyrimido(4,5-d) pyrimidone solution

A solution of 2,4,7-triamino-5-phenylpyrimido (4,5-d)pyrimidine was formulated as follows:

| | |
|---|---|
| 2,4,7-Triamino-5-phenyl-pyrimido(4,5-d)pyrimidine | 0.5% w/v |
| *Polyvinyl Pyrrolidone (molecular weight 2,500) | 50.0% w/v |
| Distilled water | to 100.0 ml. |

*The polyvinyl pyrrolidone was Kollidon PF12.

The polyvinyl pyrrolidone was dissolved in water (40 ml) and the 2,4,7-triamino-5-phenylpyrimido(4,5-d) pyrimidine was added to this solution and stirred until dissolved. The volume of the solution was adjusted to 100 ml with distilled water.

The effect of this solution on the ocular tension in the eyes of rabbits (New Zealand White/Male) was tested as described in Example 1. The mean maximum fall in ocular tension in the treated eyes was 3.1 mmHg (approximately) occuring approximately 2 hours after instillation, the untreated eyes showed a mean maximum fall of 1.6 mmHg (approximately also occurring approximately 2 hours after instillation.

The pupil diameter of both treated and untreated eye remained unchanged over the test period.

EXAMPLE 3

2,4-Diamino-6,7-dimethylpteridine suspension

A suspension of 2,4-diamino-6,7-dimethylpteridine was prepared as follows:

| 2,4-Diamino-6,7-dimethylpteridine | 0.5% w/v |
|---|---|
| *Polyvinyl pyrrolidone (Mol. wt, 2,500) | 50.0% w/v |
| Distilled water | to 100.0 ml. |

*The polyvinyl pyrrolidone was Kollidon TF12

The polyvinyl pyrrolidone was dissolved in water (40 ml) and the 2,4-diamino-6,7-dimethylpteridine suspended in this solution with stirring. The volume of the suspension was adjusted to 100 ml with distilled water with stirring.

The effect of this suspension on the ocular tension in the eyes of rabbits (New Zealand White/Male) was tested as described in Example 1. The mean maximum pressure fall in ocular tension in the treated eye for four rabbits was 1.6 mmHg. In the untreated eye no significant fall in ocular tension was shown.

The pupil diameter of both treated and untreated eyes remained unchanged over the test period.

EXAMPLE 4

2-Phenyl-4,7-diamino-6-carboxamido pteridine

A solution of 2-phenyl-4,7-diamino-6-carboxamido pteridine was prepared as follows:

| 2-Phenyl-4,7-diamino-6-carboxamido pteridine | 0.5% w/v |
|---|---|
| *Polyvinyl pyrrolidone (Mol. Wt. 2,500) | 50.0% w/v |
| Distilled water | to 100.0 ml. |

*The polyvinyl pyrrolidone was Kollidon PF12

The polyvinyl pyrrolidone was dissolved in water (40 ml) and the 2-phenyl-4,7-diamino-6-carboxamido pteridine was added and stirred until dissolved. The volume of the solution was adjusted to 100 ml with distilled water.

The effect of this solution on the ocular tension in the eyes of rabbits (New Zealand White/Male) was tested as described in Example 1. The mean maximum fall in ocular tension in the treated eye was 3.6 mmHg. The untreated eyes showed a mean maximum fall of 1.6 mmHg.

The pupil diameter of both treated and untreated eyes remained unchanged over the test period.

EXAMPLE 5

2-Phenyl-4,7-diamino-6-ethoxycarbonyl pteridine suspension

| 2-Phenyl-4,7-diamino-6-ethoxycarbonyl pteridine | 0.50% w/v |
|---|---|
| *Polyvinyl pyrrolidone (Mol. wt. 2,500) | 50.00% w/v |
| Distilled water | to 100.0 ml. |

*The polyvinyl pyrrolidone was Kollidon PF12 (Registered Trademark of BASF).

The suspension was prepared in a similar manner to that of Example 1.

The effect of this solution on the ocular tension in the eyes of rabbits (New Zealand White/Male) was tested as described in Example 1. The mean maximum fall in ocular tension in the treated eyes was 0.9 mmHg. The untreated eyes showed no corresponding fall in ocular tension.

The pupil diameter of both treated and untreated eyes remained unchanged over the test period.

EXAMPLE 6

2,4,7-Triamino-5-phenylpyrimido-(4,5-d)pyrimidinium orthophosphate Solution

| 2,4,7-Triamino-5-phenylpyrimido-(4,5-d) pyrimidinium orthophosphate | 0.5% w/v |
|---|---|
| Polyvinyl pyrrolidone (Mol. wt. 2,500) | 50.0% w/v |
| Distilled water | to 100.00 ml. |

A solution of 2,4,7-triamino-5-phenylpyrimido-(4,5-d) pyrimidinium phosphate was prepared in a similar manner to Example 2.

The effect of this solution on the ocular tension in the eyes of rabbits (New Zealand White/Male) was tested as described in Example 1. The mean maximum fall in ocular tension in the treated eyes was 2.6 mmHg. The untreated eyes showed no fall in ocular tension.

The pupil diameter of both treated and untreated eyes remained unchanged over the test period.

EXAMPLE 7

2,4,7-Triamino-6-(4-hydroxyphenyl)-pteridine suspension

A suspension of 2,4,7-triamino-6-(4-hydroxyphenyl)-pteridine is prepared as follows:

| 2,4,7-Triamino-6-(4-hydroxyphenyl)-pteridine) | 0.5% |
|---|---|
| Polyvinyl pyrrolidone (Mol. wt. 2,500) | 50.0% |
| Propylene glycol | 2.0% |
| Phenyl ethanol | 0.5% |
| Sodium hydroxide solution to adjust pH to 7 as required | |
| Distilled water | to 100 ml. |

The finely divided 2,4,7-triamino-6-(4-hydroxyphenyl)-pteridine powder is heated at 160° C. for 1 hour, sufficient for dry heat sterilisation, allowed to cool and stored under aseptic conditions.

The polyvinyl pyrrolidone, propylene glycol and phenyl ethanol are dissolved in distilled water (40 ml). The pH of this solution is adjusted to pH 7 with sodium hydroxide solution and the volume finally adjusted to 100 ml by addition of further distilled water. This solution is then sterilised by autoclaving at 116° C. for 30 minutes and then allowed to cool.

The remaining procedures are carried out in aseptic conditions under a laminar flow hood.

The sterile powder is triturated in a pestle and mortar with a portion of the sterile solution. This suspension is quantitatively added back to the bulk of the sterile solution and the whole mixed thoroughly.

The suspension is then aseptically filled into sterile amber glass bottles to provide a sterile suspension suitable for multidose application using an eye dropper.

EXAMPLE 8

2,4,7-Triamino-6-(4-nitrophenyl)-pteridine hydrochloride suspension

A suspension of 2,4,7-triamino-6-(4-nitrophenyl)-pteridine hydrochloride is formulated as follows:

| | |
|---|---|
| 2,4,7-Triamino-6-(4-nitrophenyl)-pteridine HCl | 0.5% |
| Polyvinyl pyrrolidone | 50.0% |
| Glycerol | 2.5% |
| Phenyl ethanol | 0.5% |
| Sodium hydroxide solution to adjust pH to 7 | |
| Distilled water | to 100 ml. |

The suspension is prepared and packaged using the method described in Example 7.

EXAMPLE 9

2,4,7-Triamino-6-(4-hydroxyphenyl)-pteridine hemi-sulphate ester suspension

A suspension of 2,4,7-triamino-6-(4-hydroxyphenyl)-pteridine hemi-sulphate ester is prepared as follows:

| | |
|---|---|
| 2,4,7-Triamino-6-(4-hydroxyphenyl)-pteridine hemi-sulphate ester | 0.1% |
| Sodium dihydrogen phosphate | 0.16% |
| Disodium hydrogen phosphate | 0.76% |
| Glycerol | 1.8% |
| Benzalkonium chloride | 0.01% |
| Distilled water to adjust the volume to | 100% |

The sterile, preserved, buffered suspension is prepared in a similar manner to Example 6 by bringing together the presterilised solid and liquid components into an intimate mixture.

The suspension may ba packaged in a similar manner to Example 7.

EXAMPLE 10

2,4,7-Triamino-6-(4-hydroxyphenyl)-pteridine Solution

A solution of 2,4,7-triamino-6-(4-hydroxyphenyl)-pteridine is prepared from:

| | |
|---|---|
| 2,4,7-Triamino-6-(4-hydroxyphenyl)-pteridine | 0.05% |
| Dyphylline | 6.0% |
| Benzalkonium chloride | 0.01% |
| Lactic acid solution, 10% to adjust the pH to 6 | |
| Distilled water to adjust the volume to | 100 ml. |

The dyphylline and benzalkonium chloride are dissolved in distilled water (80 ml). The 2,4,7-triamino-6-(4-hydroxyphenyl)-pteridine is added to this solution and the mixture stirred and warmed gently until the pteridine has dissolved. The solution is allowed to cool and the pH value of the solution adjusted to 6 by addition of 10% lactic acid solution. The final volume of this solution is adjusted to 100 ml by the addition of distilled water. The resultant solution is a clear liquid which is substantially isotonic with tear fluid.

This solution may be sterilised by filtration through a 0.22 micron cellulose ester membrane filter or by autoclaving at 116° C. for 30 minutes. The sterile solution may then be filled into sterile eye-dropper bottles under aseptic conditions.

EXAMPLE 11

2,4,7-Triamino-6-(4-methylphenyl)-pteridine Solution

A solution of 2,4,7-triamino-6-(4-methylphenyl)-pteridine was prepared from the following:

| | |
|---|---|
| 2,4,7-Triamino-6-(4-methylphenyl)-pteridine | 0.02% |
| Dyphylline | 6.0% |
| Potassium dihydrogen phosphate | 0.36% |
| Disodium hydrogen phosphate 2H$_2$O | 0.70% |
| Benzalkonium chloride | 0.01% |
| Distilled water to adjust the volume to | 100 ml. |

The dyphylline, potassium dihydrogen phosphate, disodium hydrogen phosphate and benzalkonium chloride are dissolved in water (80 ml). The 2,4,7-triamino-6-(4-methylphenyl)-pteridine is added to the solution and the mixture warmed to 50° C. with stirring to facilitate the dissolution of the pteridine. On cooling the volume of the solution is adjusted to 100 ml by addition of distilled water. The final solution is a clear liquid buffered at pH 7 and has a tonicity which is substantially the same as tear fluid.

This solution may be sterilised and packaged as described in Example 10.

EXAMPLE 12

2,4,7-Triamino-6-(4-hydroxyphenyl)-pteridine Solution

A solution of 2,4,7-triamino-6-(4-hydroxyphenyl)-pteridine is prepared from the following:

| | |
|---|---|
| 2,4,7-Triamino-6-(4-hydroxyphenyl)-pteridine | 0.06% |
| Proxyphylline | 6.0% |
| Potassium dihydrogen phosphate | 0.36% |
| Disodium hydrogen phosphate | 0.70% |
| Benzalkonium chloride | 0.01% |
| Distilled water to adjust the volume to | 100 ml. |

The solution is prepared in the manner described in Example 11.

The solution may be sterilised by the method described in Example 10.

DEMONSTRATION OF EFFECTIVENESS

The effect of aqueous solutions and aqueous suspensions of the tetraaza bicyclo compounds hereinbefore described on the ocular tension in the eyes of rabbits (New Zealand White/Male) was tested as follows. 50 Microliters of the tetraaza bicyclo compound composition was topically applied to one eye of the rabbit. The ocular tension of this eye was measured at 1, 2, 4 and 5 hours after the application of the composition. From the results obtained a value for the maximum mean fall in intra-ocular pressure from the group of rabbits used in each test was obtained.

| Compound | Maximum Mean Fall (mmHg) |
|---|---|
| 2,4,7-triamino-6-(2-bromo-phenyl)-pteridine (0.5% suspension in 50% polyvinyl pyrrolidone) | 3.5 |
| 2,4,7-triamino-6-(4-hydroxyphenyl)-pteridine (0.5% suspension in 50% polyvinyl pyrrolidone) | 1.4 |
| 2,4,7-triamino-6-(4-hydroxyphenyl)-pteridine, hemi-sulphate ester (0.1% suspension in 50% polyvinyl pyrrolidone) | 5.6 |
| 2,4,7-triamino-6-(4-nitrophenyl)-pteridine, hydrochloride (0.5% suspension in 50% | 3.4 |

-continued

| Compound | Maximum Mean Fall (mmHg) |
|---|---|
| polyvinyl pyrrolidone) | |
| 2,4,7-triamino-6-(4-methylphenyl)-pteridine (0.02% solution in 6% dyphylline) | 3.5 |
| 2,4-diamino-6,7 dimethyl-pteridine (0.5% suspension in 50% polyvinyl pyrrolidone) | 1.6 |
| 2-phenyl-4,7-diamino-6-carboxamido-pteridine (0.5% solution in 50% polyvinyl pyrrolidone) | 3.6 |
| 2-phenyl-4,7-diamino-6-ethoxycarbonyl-pteridine (0.5% suspension in 50% polyvinyl pyrrolidone) | 0.9 |
| 2,4,7-Triamino-5-phenylpyrimido(4,5-d)pyrimidine (0.5% solution in 50% polyvinyl pyrrolidone) | 3.2 |
| 2,4,7-Triamino-5-phenylpyrimido(4,5-d) pyrimidinium phosphate (0.5% solution in 50% polyvinyl pyrrolidone) | 2.6 |
| 2,4,7-Triamino-6-(4-hydroxyphenyl)-pteridine (0.05% solution in 6% dyphylline) | 1.4 |

A comparative study of a 0.02% aqueous suspension of 2,4,7-triamino-6-(4-methylphenyl)-pteridine containing 0.8% hydroxyethyl cellulose as suspending agent with a 0.02% aqueous solution of the same compound containing 6.0% dyphylline as solubilising agent using the method described above showed the solution caused a significant lowering of intra-ocular pressure for a longer duration than did the suspension.

What is claimed is:

1. A method for reducing the intra-ocular pressure in the eye of a patient having glaucoma which comprises topically applying of the surface of the eye a sterile composition comprising an effective intra-ocular pressure reducing amount of a compound of the formula (I):

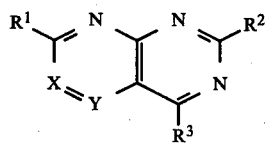

wherein X=Y is CR=N or N=CR wherein at least two of $R,R^1,R^2$ and $R^3$ are amino and the other groups of $R,R^1,R^2$ and $R^3$ are hydrogen, lower alkyl, aryl, carboxamido or lower alkoxycarbonyl, in combination with an ocularly acceptable carrier.

2. A method according to claim 1 wherein the compound is of the formula (II):

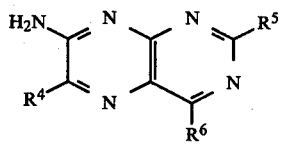

wherein one of $R^5$ and $R^6$ is amino and the other is hydrogen, lower alkyl or aryl; and $R^4$ is hydrogen, lower alkyl, aryl or carboxyamido.

3. A method for reducing the intra-ocular pressure in the eye of a patient having glaucoma which comprises topically applying to the surface of the eye a sterile composition comprising an effective intra-ocular pressure reducing amount of a compound of the formula (III):

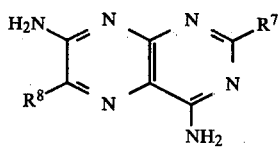

wherein $R^7$ is phenyl unsubstituted or substituted by fluoro, chloro, bromo, lower alkyl, lower alkoxy, amino, nitro, hydroxyl or sulphated hydroxyl and $R^8$ is hydrogen, lower alkyl, aryl, lower alkoxycarbonyl or carboxamido, in combination with an ocularly acceptable carrier.

4. A method for reducing the intra-ocular pressure in the eye of a patient having glaucoma which comprises topically applying to the surface of the eye a sterile composition comprising an effective intra-ocular pressure reducing amount of a compound of the formula (IV):

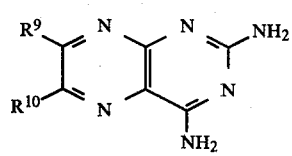

wherein $R^9$ is hydrogen, amino, lower alkyl or aryl and $R^{10}$ is hydrogen, lower alkyl, carboxyamido or phenyl unsubstituted or substituted by fluoro, chloro, bromo, lower alkyl, lower alkoxy, amino, nitro, hydroxyl or sulphated hydroxyl, in combination with an ocularly acceptable carrier.

5. A method for reducing the intra-ocular pressure in the eye of a patient having glaucoma which comprises topically applying to the surface of the eye a sterile composition comprising an effective intra-ocular pressure reducing amount of a compound of the formula (V):

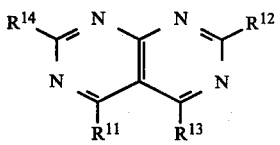

or a pharmaceutically acceptable salt thereof, wherein at least two of $R^{12}$, $R^{13}$ and $R^{14}$ are amino and the other group is hydrogen or phenyl unsubstituted or substituted by fluoro, chloro, bromo, lower alkyl, lower alkoxy, amino, nitro, hydroxyl or sulphated hydroxyl and $R^{11}$ is hydrogen or phenyl unsubstituted or substituted by fluoro, chloro, bromo, lower alkyl, lower alkoxy, amino, nitro, hydroxyl or sulphated hydroxyl, in combination with an ocularly acceptable carrier.

6. A method according to claim 5 in which the pharmaceutically acceptable salt is selected from the group consisting of the hydrochloride, sulphate, ortho phosphate, acetate, gluconate, glutamate and lactate.

7. A method according to claim 1 wherein the compound is 2-phenyl-4,7-diamino-6-carboxamido-pteridine, the ethyl ester of 2-phenyl-4,7-diamino-pteridine-6-carboxylic acid, 2,4,7-triamino-5-phenylpyrimido(4,5-d)pyrimidine or 2,4,7-triamino-5-phenylpyrimido(4,5-d)pyrimidinium orthophosphate.

8. A method according to claim 4 wherein the compound is 2,4,7-triamino-6-(2-bromophenyl)-pteridine, 2,4,7-triamino-6-(4-hydroxyphenyl)-pteridine, the hemi sulphate ester of 2,4,7-triamino-6-(4-hydroxy phenyl)-pteridine, or 2,4-diamino-6,7-dimethyl pteridine.

9. A method according to claim 1 in which the composition is in the form of an aqueous suspension.

10. A method according to claim 9 in which the composition contains from 0.01 to 5% of a compound of formula (I).

11. A method according to claim 9 in which the composition contains from 0.05 to 2.5% of a compound of formula (I).

12. A method according to claim 9 in which the composition contains from 0.1 to 1% of a compound of formula (I).

13. A method according to claim 9 in which the composition contains from 0.1 to 10% of a cellulosic derivative as a suspending agent for a compound of formula (I).

14. A method according to claim 9 in which the composition contains from 0.25 to 2.5% of a cellulosic derivative as a suspending agent for a compound of formula (I).

15. A method according to claim 13 in which the cellulosic derivative is hydroxyethyl cellulose.

16. A method according to claim 9 in which the suspending agent is a polysaccharide derivative or a water soluble polymer.

17. A method according to claim 9 in which the composition contains from 0.01 to 5% of a surface active agent.

18. A method according to claim 9 in which the composition contains from 0.02 to 0.2% of a surface active agent.

19. A method according to claim 9 in which the surface active agent is a polyoxyethylated sorbitan fatty acid ester or a polyoxypropylene-polyoxyethylene diol block copolymer.

20. A method according to claim 1 in which the composition is in the form of an aqueous solution.

21. A method according to claim 20 in which the composition contains a solubilizing agent for a compound of formula (I).

22. A method according to claim 20 in which the composition contains from 0.01 to 2% of a compound of formula (I).

23. A method according to claim 21 in which the solubilizing agent is polyvinyl pyrrolidone, polyalkylene glycol or a non-ionic surfactant or a combination of two or three of such agents.

24. A method according to claim 23 in which the composition contains from 15 to 52% of a polyvinyl pyrrolidone which has a molecular weight of less than 40,000 as solubilizing agent.

25. A method according to claim 21 in which the composition contains from 0.1 to 10% of a water soluble xanthine as the solubilizing agent.

26. A method according to claim 21 in which the composition contains from 2 to 7.5% of a water soluble xanthine as the solubilizing agent.

27. A method according to claim 25 in which the water soluble xanthine is proxyphylline.

28. A method according to claim 25 in which the water soluble xanthine is dyphylline.

29. A method according to claim 1 in which the composition is rendered substantially isotonic.

30. A method according to claim 1 in which the pH of the composition is 6.0 to 8.5.

31. A method according to claim 25 in which the composition contains a buffer to give the composition a pH of between 5.0 and 8.0.

32. A method according to claim 1 in which the composition contains an effective amount of preservative.

33. A method according to claim 32 in which the preservative is benzalkonium chloride.

34. A method according to claim 33 in which the composition contains from 0.005 to 0.04% benzalkonium chloride.

35. A method according to claim 1 in which the composition is in the form of a soluble ocular implant.

36. A method according to claim 1 in which the composition is in the form of an ophthalmic ointment.

37. A sterile pharmaceutical composition for reducing the intra-ocular pressure in the eye of a patient having glaucoma adapted for topical application to the eye which comprises an effective intra-ocular pressure reducing amount of a compound of formula (I):

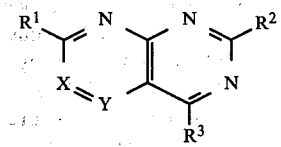

wherein X=Y is CR=N or N=CR wherein at least two of $R, R^1, R^2$ and $R^3$ are amino and the other groups of $R, R^1, R^2$ and $R^3$ are hydrogen, lower alkyl, aryl, carboxamido or lower alkoxycarbonyl, in combination with an ocularly acceptable carrier.

38. A composition according to claim 37 wherein the compound is of the formula (II):

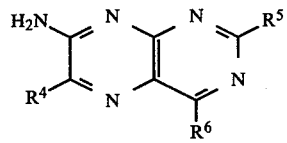

wherein one of $R^5$ and $R^6$ is amino and the other is hydrogen, lower alkyl or aryl; and $R^4$ is hydrogen, lower alkyl, aryl or carboxyamido.

39. A sterile pharmaceutical composition for reducing the intra-ocular pressure in the eye of a patient having glaucoma adapted for topical application to the eye which comprises an effective intra-ocular pressure reducing amount of a compound of the formula (III):

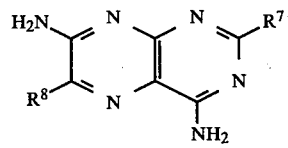

wherein $R^7$ is phenyl unsubstituted or substituted by fluoro, chloro, bromo, lower alkyl, lower alkoxy, amino, nitro, hydroxyl or sulphated hydroxyl and $R^8$ is hydrogen, lower alkyl, aryl, lower alkoxycarbonyl or carboxamido, in combination with an ocularly acceptable carrier.

40. A sterile pharmaceutical composition for reducing the intra-ocular pressure in the eye of a patient having glaucoma adapted for topical application to the eye which comprises an effective intra-ocular pressure reducing amount of a compound of the formula (IV):

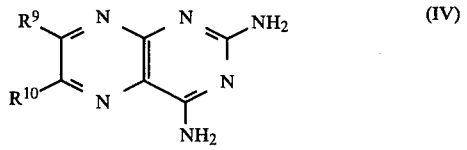 (IV)

wherein $R^9$ is hydrogen, amino, lower alkyl or aryl and $R^{10}$ is hydrogen, lower alkyl, carboxyamido or phenyl unsubstituted or substituted by fluoro, chloro, bromo, lower alkyl, lower alkoxy, amino, nitro, hydroxyl or sulphated hydroxyl, in combination with an ocularly acceptable carrier.

41. A sterile pharmaceutical composition for reducing the intra-ocular pressure in the eye of a patient having glaucoma adapted for topical application to the eye which comprises an effective intra-ocular pressure reducing amount of a compound of the formula (V):

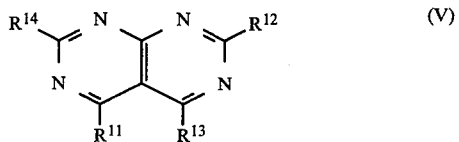 (V)

or a pharmaceutically acceptable salt thereof, wherein at least two of $R^{12}$, $R^{13}$ and $R^{14}$ are amino and the other group is hydrogen or phenyl unsubstituted or substituted by fluoro, chloro, bromo, lower alkyl, lower alkoxy, amino, nitro, hydroxyl or sulphated hydroxyl and $R^{11}$ is hydrogen or phenyl unsubstituted or substituted by fluoro, chloro, bromo, lower alkyl, lower alkoxy, amino, nitro, hydroxyl or sulphated hydroxyl, in combination with an ocularly acceptable carrier.

42. A composition according to claim 41 in which the pharmaceutically acceptable salt is selected from the group consisting of the hydrochloride, sulphate, orthophosphate, acetate, gluconate, glutamate and lactate.

43. A composition according to claim 37 wherein the compound is 2-phenyl-4,7-diamino-6-carboxamido-pteridine, the ethyl ester of 2-phenyl-4,7-diamino-pteridine-6-carboxylic acid, 2,4,7-triamino-5-phenyl-pyrimido(4,5-d)pyrimidine or 3,4,7-triamino-5-phenyl-pyrimido(4,5-d)pyrimidinium orthophosphate.

44. A composition according to claim 40 wherein the compound is 2,4,7-triamino-6-(2-bromophenyl)-pteridine, 2,4,7-triamino-6-(4-hydroxyphenyl)-pteridine, the hemi sulphate ester of 2,4,7-triamino-6-(4-hydroxy phenyl)-pteridine, or 2,4-diamino-6,7-dimethyl pteridine.

45. A composition according to claim 37 in which the composition is in the form of an aqueous suspension.

46. A composition according to claim 45 in which the composition contains from 0.01 to 5% of a compound of formula (I).

47. A composition according to claim 45 in which the composition contains a suspending agent selected from the group consisting of a cellulosic derivative, a polysaccharide derivative or a water soluble polymer.

48. A composition according to claim 47 in which the composition contains from 0.1 to 10% of a cellulose derivative as a suspending agent for a compound formula (I).

49. A composition according to claim 45 in which the composition contains from 0.01 to 5% of a surface active agent.

50. A composition according to claim 49 in which the surface active agent is a polyoxyethylated sorbitan fatty acid ester or a polyoxypropylene-polyoxyethylene diol block copolymer.

51. A composition according to claim 37 in which the composition is in the form of an aqueous solution.

52. A composition according to claim 51 in which the composition contains a solubilizing agent for a compound of formula (I).

53. A composition according to claim 52 in which the composition contains from 0.01 to 2% of a compound of formula (I).

54. A composition according to claim 52 in which the solubilizing agent is polyvinyl pyrrolidone, polyalkylene glycol or a non-ionic surfactant or a combination of two or three of such agents.

55. A composition according to claim 52 in which the composition contains from 0.1 to 10% of a water soluble xanthine as the solubilizing agent.

56. A composition according to claim 37 in which the composition is rendered substantially isotonic.

57. A composition according to claim 37 in which the pH of the composition is 6.0 to 8.5.

58. A composition according to claim 37 in which the composition contains an effective amount of a preservative.

59. A composition according to claim 58 in which the composition contains from 0.005 to 0.04% of benzalkonium chloride as preservative.

60. A composition according to claim 37 in which the composition is in the form of a soluble ocular implant.

61. A composition according to claim 37 in which the composition is in the form of an ophthalmic ointment.

* * * * *

UNITED STATES PATENT AND TRADEMARK OFFICE
CERTIFICATE OF CORRECTION

PATENT NO. : 4,425,346
DATED : January 10, 1984
INVENTOR(S) : MICHAEL HORLINGTON It is certified that error appears in the above-identified patent and that said Letters Patent are hereby corrected as shown below:

Page 1, change the Foreign Application Priority Data to read as follows:

[30]         Foreign Application Priority Data

| Aug. 1, 1980 | [GB] | United Kingdom | 8025286 |
| Jan. 8, 1981 | [GB] | United Kingdom | 8100521 |
| Feb. 9, 1981 | [GB] | United Kingdom | 8103917 |
| Mar. 18, 1981 | [GB] | United Kingdom | 8108537 |
| Apr. 2, 1981 | [GB] | United Kingdom | 8110448 |
| July 21, 1981 | [GB] | United Kingdom | 8122410 |
| July 28, 1981 | [GB] | United Kingdom | 8123222 |

Column 1, line 22, "optical" should read --topical--.

Signed and Sealed this

Twenty-third Day of October 1984

[SEAL]

Attest:

Attesting Officer

GERALD J. MOSSINGHOFF
Commissioner of Patents and Trademarks